(12) United States Patent
Desjardin et al.

(10) Patent No.: US 11,786,233 B2
(45) Date of Patent: Oct. 17, 2023

(54) RETENTION ANCHOR WITH SUTURE TIE DOWN FOR SURGICAL ACCESS DEVICES

(71) Applicant: Covidien LP, Mansfield, MA (US)

(72) Inventors: Kevin Desjardin, Prospect, CT (US); Douglas M. Pattison, East Hartford, CT (US); Oksana Buyda, East Haven, CT (US); Christopher A. Tokarz, Torrington, CT (US); Astley C. Lobo, West Haven, CT (US); Amanda M. Adinolfi, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 554 days.

(21) Appl. No.: 16/832,003

(22) Filed: Mar. 27, 2020

(65) Prior Publication Data

US 2021/0298737 A1  Sep. 30, 2021

(51) Int. Cl.
  *A61B 17/04* (2006.01)
  *A61B 17/34* (2006.01)

(52) U.S. Cl.
  CPC ...... *A61B 17/0401* (2013.01); *A61B 17/3421* (2013.01); *A61B 17/3423* (2013.01);
  (Continued)

(58) Field of Classification Search
  CPC ........ A61B 17/3421; A61B 2017/3419; A61B 2017/3492; A61B 17/3423–2017/3429;
  (Continued)

(56) References Cited

U.S. PATENT DOCUMENTS

| 397,060 A | 1/1889 | Knapp |
| 512,456 A | 1/1894 | Sadikova |

(Continued)

FOREIGN PATENT DOCUMENTS

| EP | 0480653 A1 | 4/1992 |
| EP | 0610099 A2 | 8/1994 |

(Continued)

OTHER PUBLICATIONS

Extended European Search Report dated Aug. 6, 2021 issued in corresponding EP Appln. No. 21165280.5.
(Continued)

*Primary Examiner* — Tan-Uyen T Ho
*Assistant Examiner* — Charles M Wei
(74) *Attorney, Agent, or Firm* — Carter, DeLuca & Farrell LLP

(57) ABSTRACT

A surgical access assembly includes a cannula including an elongated shaft and a retention anchor movably positionable along the elongated shaft. The retention anchor includes an annular body and a fixation body. The annular body includes a proximally-facing surface, a distally-facing surface, an inner side surface defining an opening therethrough, and an outer side surface. The fixation body includes a disc secured to the distally-facing surface of the annular body and wings extending radially outwardly from the disc beyond the outer side surface of the annular body. The disc defines an opening therethrough and the elongated shaft extends through the openings in the annular body and the fixation body.

20 Claims, 4 Drawing Sheets

(52) U.S. Cl.
CPC ............. *A61B 2017/0404* (2013.01); *A61B 2017/0427* (2013.01); *A61B 2017/3419* (2013.01); *A61B 2017/3492* (2013.01)

(58) Field of Classification Search
CPC .......... A61M 2039/0223; A61M 25/02; A61M 2025/0286; A61M 2039/0261
See application file for complete search history.

(56) References Cited

U.S. PATENT DOCUMENTS

| | | | |
|---|---|---|---|
| 1,213,005 A | 1/1917 | Pillsbury | |
| 2,912,981 A | 11/1959 | Keough | |
| 2,936,760 A | 5/1960 | Gains | |
| 3,039,468 A | 6/1962 | Price | |
| 3,050,066 A | 8/1962 | Koehn | |
| 3,253,594 A | 5/1966 | Matthews et al. | |
| 3,397,699 A | 8/1968 | Kohl | |
| 3,545,443 A | 12/1970 | Ansari et al. | |
| 3,713,447 A | 1/1973 | Adair | |
| 3,774,596 A | 11/1973 | Cook | |
| 3,800,788 A | 4/1974 | White | |
| 3,882,852 A | 5/1975 | Sinnreich | |
| 3,896,816 A | 7/1975 | Mattler | |
| 3,961,632 A | 6/1976 | Moossun | |
| RE29,207 E | 5/1977 | Bolduc et al. | |
| 4,083,369 A | 4/1978 | Sinnreich | |
| 4,217,889 A | 8/1980 | Radovan et al. | |
| 4,243,050 A | 1/1981 | Littleford | |
| 4,276,874 A | 7/1981 | Wolvek et al. | |
| 4,312,353 A | 1/1982 | Shahbabian | |
| 4,327,709 A | 5/1982 | Hanson et al. | |
| 4,345,606 A | 8/1982 | Littleford | |
| 4,411,654 A | 10/1983 | Boarini et al. | |
| 4,416,267 A | 11/1983 | Garren et al. | |
| 4,490,137 A | 12/1984 | Moukheibir | |
| 4,496,345 A | 1/1985 | Hasson | |
| 4,574,806 A | 3/1986 | McCarthy | |
| 4,581,025 A | 4/1986 | Timmermans | |
| 4,596,554 A | 6/1986 | Dastgeer | |
| 4,596,559 A | 6/1986 | Fleischhacker | |
| 4,608,965 A | 9/1986 | Anspach, Jr. et al. | |
| 4,644,936 A | 2/1987 | Schiff | |
| 4,654,030 A | 3/1987 | Moll et al. | |
| 4,685,447 A | 8/1987 | Iversen et al. | |
| 4,701,163 A | 10/1987 | Parks | |
| 4,738,666 A | 4/1988 | Fuqua | |
| 4,769,038 A | 9/1988 | Bendavid et al. | |
| 4,772,266 A | 9/1988 | Groshong | |
| 4,779,611 A | 10/1988 | Grooters et al. | |
| 4,784,133 A | 11/1988 | Mackin | |
| 4,793,348 A | 12/1988 | Palmaz | |
| 4,798,205 A | 1/1989 | Bonomo et al. | |
| 4,800,901 A | 1/1989 | Rosenberg | |
| 4,802,479 A | 2/1989 | Haber et al. | |
| 4,813,429 A | 3/1989 | Eshel et al. | |
| 4,840,613 A | 6/1989 | Balbierz | |
| 4,854,316 A | 8/1989 | Davis | |
| 4,861,334 A | 8/1989 | Nawaz | |
| 4,865,593 A | 9/1989 | Ogawa et al. | |
| 4,869,717 A | 9/1989 | Adair | |
| 4,888,000 A | 12/1989 | McQuilkin et al. | |
| 4,897,082 A * | 1/1990 | Erskine ............. | A61M 25/02 604/177 |
| 4,899,747 A | 2/1990 | Garren et al. | |
| 4,917,668 A | 4/1990 | Haindl | |
| 4,931,042 A | 6/1990 | Holmes et al. | |
| 4,955,895 A | 9/1990 | Sugiyama et al. | |
| 5,002,557 A | 3/1991 | Hasson | |
| 5,009,643 A | 4/1991 | Reich et al. | |
| 5,030,206 A | 7/1991 | Lander | |
| 5,030,227 A | 7/1991 | Rosenbluth et al. | |
| 5,074,871 A | 12/1991 | Groshong | |
| 5,098,392 A | 3/1992 | Fleischhacker et al. | |
| 5,104,383 A | 4/1992 | Shichman | |
| 5,116,318 A | 5/1992 | Hillstead | |
| 5,116,357 A | 5/1992 | Eberbach | |
| 5,122,122 A | 6/1992 | Allgood | |
| 5,122,155 A | 6/1992 | Eberbach | |
| 5,137,512 A | 8/1992 | Burns et al. | |
| 5,141,494 A | 8/1992 | Danforth et al. | |
| 5,141,515 A | 8/1992 | Eberbach | |
| 5,147,302 A | 9/1992 | Euteneuer et al. | |
| 5,147,316 A | 9/1992 | Castillenti | |
| 5,147,374 A | 9/1992 | Fernandez | |
| 5,158,545 A | 10/1992 | Trudell et al. | |
| 5,159,925 A | 11/1992 | Neuwirth et al. | |
| 5,163,949 A | 11/1992 | Bonutti | |
| 5,176,692 A | 1/1993 | Wilk et al. | |
| 5,176,697 A | 1/1993 | Hasson et al. | |
| 5,183,463 A | 2/1993 | Debbas | |
| 5,188,596 A | 2/1993 | Condon et al. | |
| 5,188,630 A | 2/1993 | Christoudias | |
| 5,195,507 A | 3/1993 | Bilweis | |
| 5,201,742 A | 4/1993 | Hasson | |
| 5,201,754 A | 4/1993 | Crittenden et al. | |
| 5,209,725 A | 5/1993 | Roth | |
| 5,215,526 A | 6/1993 | Deniega et al. | |
| 5,222,970 A | 6/1993 | Reeves | |
| 5,226,890 A | 7/1993 | Ianniruberto et al. | |
| 5,232,446 A | 8/1993 | Arney | |
| 5,232,451 A | 8/1993 | Freitas et al. | |
| 5,234,454 A | 8/1993 | Bangs | |
| 5,250,025 A | 10/1993 | Sosnowski et al. | |
| 5,258,026 A | 11/1993 | Johnson et al. | |
| 5,269,753 A | 12/1993 | Wilk | |
| 5,290,249 A | 3/1994 | Foster et al. | |
| 5,308,327 A | 5/1994 | Heaven et al. | |
| 5,309,896 A | 5/1994 | Moll et al. | |
| 5,314,443 A | 5/1994 | Rudnick | |
| 5,318,012 A | 6/1994 | Wilk | |
| 5,330,497 A | 7/1994 | Freitas et al. | |
| 5,342,307 A | 8/1994 | Euteneuer et al. | |
| 5,346,504 A | 9/1994 | Ortiz et al. | |
| 5,359,995 A | 11/1994 | Sewell, Jr. | |
| 5,361,752 A | 11/1994 | Moll et al. | |
| 5,370,134 A | 12/1994 | Chin et al. | |
| 5,383,889 A | 1/1995 | Warner et al. | |
| 5,397,311 A | 3/1995 | Walker et al. | |
| 5,402,772 A | 4/1995 | Moll et al. | |
| 5,407,433 A | 4/1995 | Loomas | |
| 5,431,173 A | 7/1995 | Chin et al. | |
| 5,445,615 A | 8/1995 | Yoon | |
| 5,468,248 A | 11/1995 | Chin et al. | |
| 5,514,091 A | 5/1996 | Yoon | |
| 5,514,153 A | 5/1996 | Bonutti | |
| 5,540,658 A | 7/1996 | Evans et al. | |
| 5,540,711 A | 7/1996 | Kieturakis et al. | |
| 5,607,441 A | 3/1997 | Sierocuk et al. | |
| 5,607,443 A | 3/1997 | Kieturakis et al. | |
| 5,632,761 A | 5/1997 | Smith et al. | |
| 5,656,013 A | 8/1997 | Yoon | |
| 5,667,479 A | 9/1997 | Kieturakis | |
| 5,667,520 A | 9/1997 | Bonutti | |
| 5,704,372 A | 1/1998 | Moll et al. | |
| 5,707,382 A | 1/1998 | Sierocuk et al. | |
| 5,713,869 A | 2/1998 | Morejon | |
| 5,722,986 A | 3/1998 | Smith et al. | |
| 5,728,119 A | 3/1998 | Smith et al. | |
| 5,730,748 A | 3/1998 | Fogarty et al. | |
| 5,730,756 A | 3/1998 | Kieturakis et al. | |
| 5,738,628 A | 4/1998 | Sierocuk et al. | |
| 5,755,693 A | 5/1998 | Walker et al. | |
| 5,762,604 A | 6/1998 | Kieturakis | |
| 5,772,680 A | 6/1998 | Kieturakis et al. | |
| 5,779,728 A | 7/1998 | Lunsford et al. | |
| 5,792,112 A * | 8/1998 | Hart ................... | A61B 17/3417 604/185 |
| 5,797,947 A | 8/1998 | Mollenauer | |
| 5,803,901 A | 9/1998 | Chin et al. | |
| 5,810,867 A | 9/1998 | Zarbatany et al. | |
| 5,814,021 A * | 9/1998 | Balbierz ............. | A61M 25/02 604/174 |
| 5,814,060 A | 9/1998 | Fogarty et al. | |

(56) References Cited

U.S. PATENT DOCUMENTS

| | | | |
|---|---|---|---|
| 5,836,913 | A | 11/1998 | Orth et al. |
| 5,836,961 | A | 11/1998 | Kieturakis et al. |
| 5,865,802 | A | 2/1999 | Yoon et al. |
| 5,893,866 | A | 4/1999 | Hermann et al. |
| 5,925,058 | A | 7/1999 | Smith et al. |
| 6,361,543 | B1 | 3/2002 | Chin et al. |
| 6,368,337 | B1 | 4/2002 | Kieturakis et al. |
| 6,375,665 | B1 | 4/2002 | Nash et al. |
| 6,379,372 | B1 | 4/2002 | Dehdashtian et al. |
| 6,432,121 | B1 | 8/2002 | Jervis |
| 6,447,529 | B2 | 9/2002 | Fogarty et al. |
| 6,468,205 | B1 | 10/2002 | Mollenauer et al. |
| 6,482,175 | B1 * | 11/2002 | Walker ............... A61B 17/3415 604/116 |
| 6,506,200 | B1 | 1/2003 | Chin |
| 6,514,272 | B1 | 2/2003 | Kieturakis et al. |
| 6,517,514 | B1 | 2/2003 | Campbell |
| 6,527,787 | B1 | 3/2003 | Fogarty et al. |
| 6,540,764 | B1 | 4/2003 | Kieturakis et al. |
| 6,554,802 | B1 * | 4/2003 | Pearson ................ A61M 25/02 604/177 |
| 6,796,960 | B2 | 9/2004 | Cioanta et al. |
| 7,691,089 | B2 * | 4/2010 | Gresham ............ A61B 17/3417 604/174 |
| 8,277,418 | B2 * | 10/2012 | Lopez ................ A61B 17/3462 604/165.04 |
| 8,343,106 | B2 * | 1/2013 | Lopez ..................... A61F 9/007 604/164.08 |
| 8,454,645 | B2 | 6/2013 | Criscuolo et al. |
| 10,987,128 | B2 * | 4/2021 | Buyda ................ A61B 17/3415 |
| 2004/0111061 | A1 * | 6/2004 | Curran ............... A61B 17/3421 604/174 |
| 2004/0138702 | A1 * | 7/2004 | Peartree ................... B25B 5/12 606/213 |
| 2005/0192594 | A1 * | 9/2005 | Skakoon ................ A61B 90/50 606/129 |
| 2006/0142699 | A1 * | 6/2006 | Lampropoulos .. A61M 25/0097 604/164.04 |
| 2008/0275401 | A1 * | 11/2008 | Sage .................. A61M 25/0612 604/175 |
| 2009/0182282 | A1 * | 7/2009 | Okihisa .............. A61B 17/3423 604/165.01 |
| 2009/0287155 | A1 * | 11/2009 | Silich .................... A61M 25/02 604/174 |
| 2011/0144447 | A1 * | 6/2011 | Schleitweiler ..... A61B 17/3421 600/210 |
| 2018/0271557 | A1 * | 9/2018 | Buyda ................ A61B 17/3421 |
| 2019/0060637 | A1 * | 2/2019 | Duijsens .............. A61N 1/0539 |

FOREIGN PATENT DOCUMENTS

| | | |
|---|---|---|
| EP | 0880939 A1 | 12/1998 |
| EP | 3378422 A2 | 9/2018 |
| WO | 9206638 A1 | 4/1992 |
| WO | 9218056 A1 | 10/1992 |
| WO | 9221293 A1 | 12/1992 |
| WO | 9221295 A1 | 12/1992 |
| WO | 9309722 A1 | 5/1993 |
| WO | 9714458 A1 | 4/1997 |
| WO | 9721461 A1 | 6/1997 |
| WO | 9912602 A1 | 3/1999 |
| WO | 0126724 A2 | 4/2001 |
| WO | 02096307 A2 | 12/2002 |
| WO | 2004032756 A2 | 4/2004 |
| WO | 2018128644 A1 | 7/2018 |

OTHER PUBLICATIONS

Communication Pursuant to Article 94(3) EPC issued in corresponding European Application No. 21 165 280.5 dated Sep. 8, 2022, 6 pages.

* cited by examiner

RETENTION ANCHOR WITH SUTURE TIE DOWN FOR SURGICAL ACCESS DEVICES

FIELD

The present disclosure relates generally to surgical access devices. In particular, the present disclosure relates to retention anchors with a suture tie down for fixing surgical access devices in tissue.

BACKGROUND

In minimally invasive surgical procedures, including endoscopic and laparoscopic surgeries, a surgical access device permits the introduction of a variety of surgical instruments into a body cavity or opening. A surgical access device (e.g., a cannula or an access port) is introduced through an opening in tissue (e.g., a naturally occurring orifice or an incision) to provide access to an underlying surgical site in the body. The opening is typically made using an obturator having a blunt or sharp tip that may be inserted through a passageway of the surgical access device. For example, a cannula has a tube of rigid material with a thin wall construction, through which an obturator may be passed. The obturator is utilized to penetrate a body wall, such as an abdominal wall, or to introduce the surgical access device through the body wall, and is then removed to permit introduction of surgical instruments through the surgical access device to perform the surgical procedure.

Minimally invasive surgical procedures, including both endoscopic and laparoscopic procedures, permit surgery to be performed on organs, tissues, and vessels far removed from an opening within the tissue. In laparoscopic procedures, the abdominal cavity is insufflated with an insufflation gas, e.g., $CO_2$, to create a pneumoperitoneum thereby providing access to the underlying organs. A laparoscopic instrument is introduced through a cannula into the abdominal cavity to perform one or more surgical tasks. The cannula may incorporate a seal to establish a substantially fluid tight seal about the laparoscopic instrument to preserve the integrity of the pneumoperitoneum. The cannula, which is subjected to the pressurized environment, e.g., the pneumoperitoneum, may include an anchor mechanism to prevent the cannula from backing out of the opening in the abdominal wall, for example, during withdrawal of the laparoscopic instrument from the cannula. The cannula may also include a retention mechanism to prevent the cannula for being over-inserted into the abdominal wall, for example, during insertion of the laparoscopic instrument into the cannula.

SUMMARY

This disclosure generally relates to a retention anchor for securing a surgical access device within tissue. The retention anchor provides a counter force during insertion and/or articulation of surgical instruments through the surgical access device. In aspects in which the surgical access device includes an anchor mechanism, the retention anchor is utilized in conjunction with the anchor mechanism to limit longitudinal movement of the surgical access device relative to the tissue (e.g., retropulsion and over-insertion) during, for example, receipt, manipulation, and/or withdrawal of surgical instruments therethrough.

The retention anchor includes an annular body, a fixation body, and optionally, a compressible collar. The annular body provides a holding force on a surgical access device, the fixation body secures the retention anchor to the tissue through which the surgical access device is disposed, and the compressible collar assists with sealing the opening into the tissue and minimizing port site trauma.

In one aspect, the disclosure provides a surgical access assembly including a cannula having an elongated shaft and a retention anchor movably positioned along the elongated shaft. The retention anchor includes an annular body and a fixation body. The annular body includes a proximally-facing surface, a distally-facing surface, an inner side surface defining an opening therethrough, and an outer side surface. The fixation body includes a disc secured to the distally-facing surface of the annular body and wings extending radially outwardly from the disc beyond the outer side surface of the annular body. The disc defines an opening therethrough and the elongated shaft extends through the openings in the annular body and the fixation body.

The inner side surface of the annular body may frictionally engage the elongated shaft of the cannula. The inner side surface may include ridges.

Each wing of the fixation body may include a notch defined in a proximal facing surface thereof and/or a flange disposed at a terminal end thereof. A distal surface of the fixation body may be planar.

The retention anchor may further include a compressible collar secured to a distal surface of the fixation body. The compressible collar may have an expanded configuration and a compressed configuration. The compressible collar may extend radially outwardly of the first annular body and be concentric therewith. Each wing of the fixation body may include a notch defined in a proximal facing surface thereof, and the compressible collar may be disposed radially inwardly of the notches.

In another aspect, the disclosure provides a retention anchor for a surgical access device including an annular body and a fixation body. The annular body includes a proximally-facing surface, a distally-facing surface, an inner side surface defining an opening therethrough, and an outer side surface. The fixation body includes a disc secured to the distally-facing surface of the annular body and wings extending radially outwardly from the disc beyond the outer side surface of the annular body. The disc defines an opening therethrough and the elongated shaft extends through the openings in the annular body and the fixation body.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
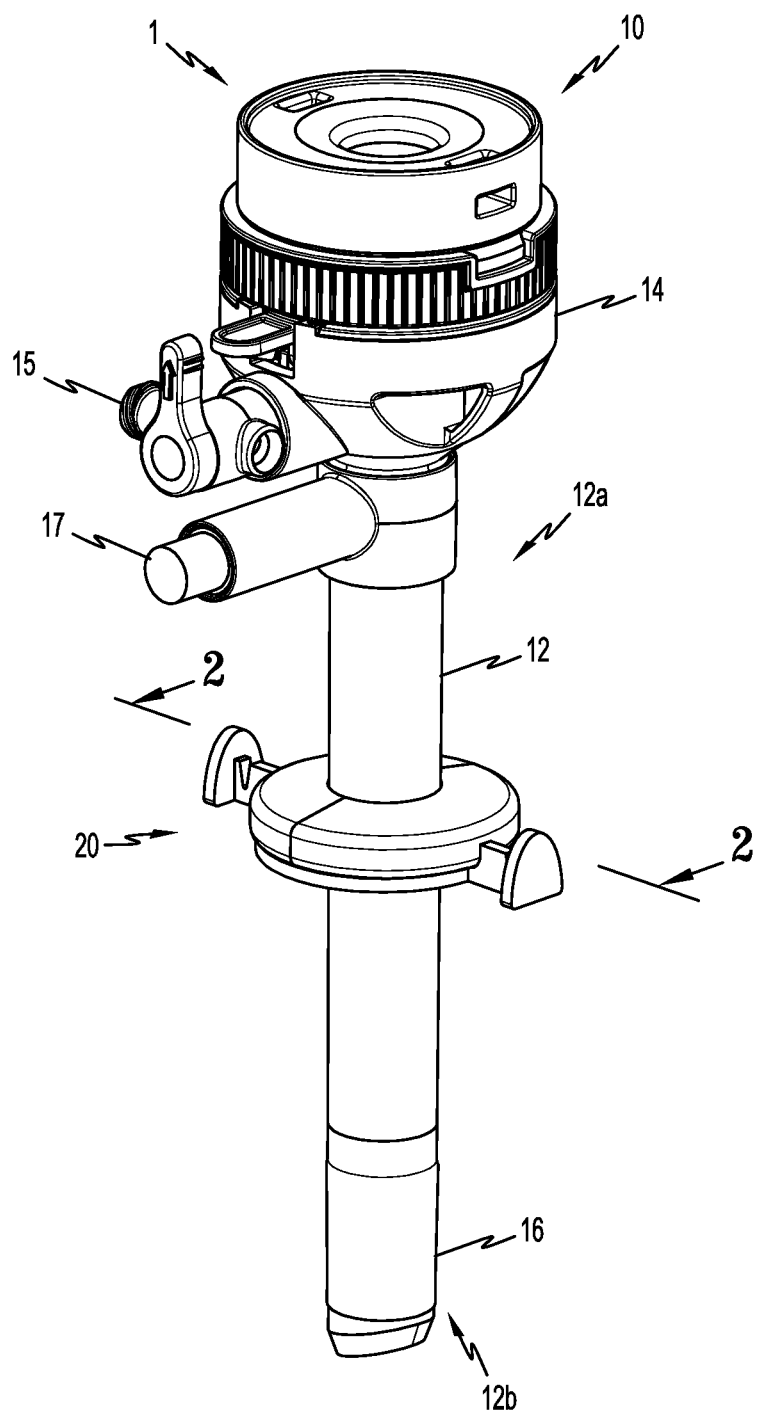
FIG. 1 is a perspective view of a surgical access assembly including a cannula and a retention anchor in accordance with an aspect of the disclosure.

Aspects of the disclosure are described hereinbelow with reference to the accompanying drawings; however, it is to be understood that the disclosed aspects are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

Like reference numerals refer to similar or identical elements throughout the description of the figures. Throughout this description, the term "proximal" refers to a portion of a structure, or component thereof, that is closer to a user, and the term "distal" refers to a portion of the structure, or component thereof, that is farther from the user.

FIG. 1 illustrates a surgical access assembly 1 including a surgical access device or cannula 10 and a retention anchor 20. The cannula 10 generally includes an elongated shaft 12 supporting an instrument housing 14 on a proximal or first end portion 12a thereof and an expandable anchor 16 (e.g., an inflatable anchor, such as a balloon, or a contractable anchor, such as a collapsible flange) on a distal or second end portion 12b thereof. The expandable anchor 16 secures the cannula 10 against an inner surface of tissue, such as an abdominal wall (see e.g., FIG. 7).

The retention anchor 20 is supported on the elongated shaft 12 of the cannula 10. The retention anchor 20 is releasably engageable with the elongated shaft 12, and slidable therealong to adjust the position of the retention anchor 20 on the elongated shaft 12. The retention anchor 20 secures the cannula 10 against an outer surface of the tissue (see e.g., FIG. 7) and stabilizes the cannula 10 relative to the tissue.

Generally, the cannula 10 is employed during surgery (e.g., laparoscopic surgery) to access a surgical site and may, in various aspects, provide for the sealed access of surgical instruments into an insufflated body cavity, such as an abdominal cavity. The instrument housing 14 of the cannula 10 may include an insufflation port 15 that provides insufflation fluid (e.g., gases) into the body cavity, seals and/or valves (not shown) that allows surgical instrument to be inserted into the body cavity while preventing the escape of the insufflation fluid therefrom, and an anchor inflation port 17 which is in fluid communication with the expandable anchor 16 to expand and/or contract the expandable anchor 16.

The cannula 10 is usable with an obturator (not shown). The obturator generally includes an elongated body supporting a tip on a distal end thereof. The tip can have a bladed or non-bladed (e.g., blunt) penetrating distal end that can be used to incise or separate tissue of a body wall so that the cannula 10 can be introduced therethrough. The cannula 10 and the obturator may be capable of being selectively connected together. For example, the obturator may be inserted into and through the cannula 10 until a handle housing of the obturator engages, e.g., selectively locks into, the instrument housing 14 of the cannula 10. In this initial position, the cannula 10 and the obturator, which together form a trocar assembly, are employed to tunnel through a body wall, e.g., an abdominal wall, either by making a new passage through the body wall or by passing through an existing opening through the body wall. Once the trocar assembly has tunneled through the body wall, the obturator is removed, leaving the cannula 10 in place, e.g., in an incision created by the trocar assembly.

For a detailed description of the structure and function of exemplary surgical access devices suitable for use with a retention anchor of the present disclosure, reference may be made to U.S. Pat. Nos. 7,691,089; 8,926,508; and 10,299,778, the entire contents of each of which are hereby incorporated by reference herein.

Figure 2:
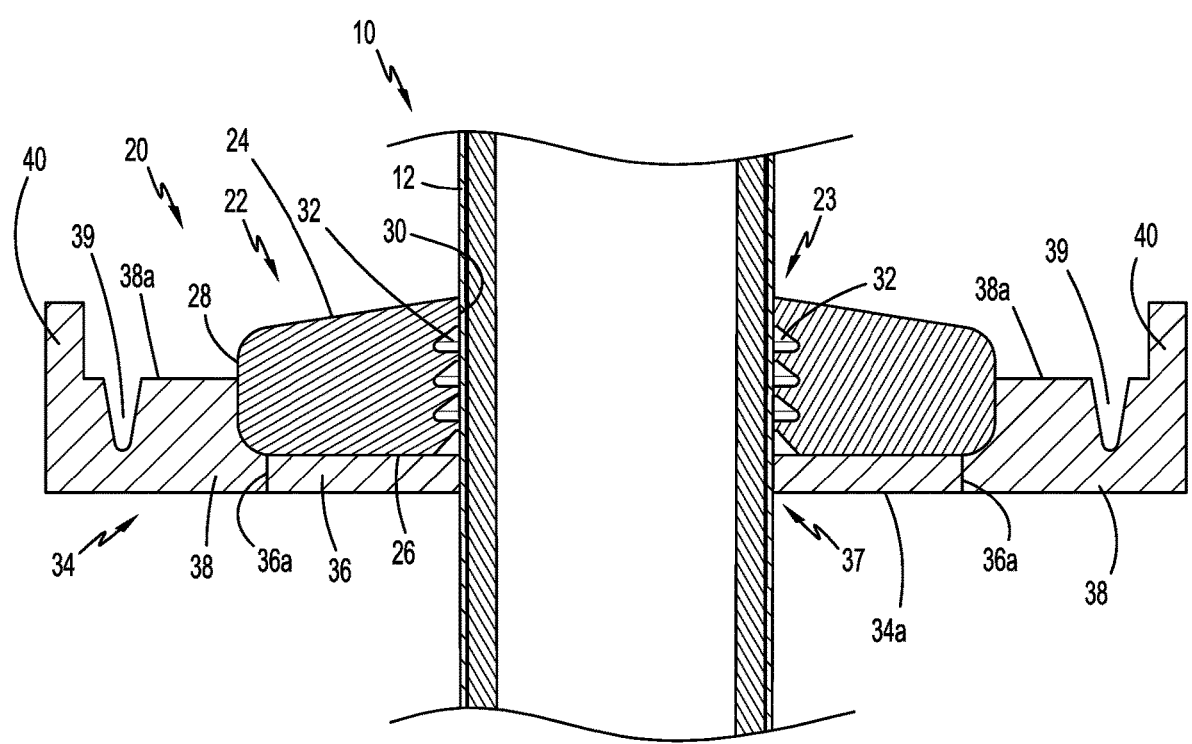
FIG. 2 is cross-sectional view of the surgical access assembly of FIG. 1, taken along section line 2-2 of FIG. 1.
Figure 3:
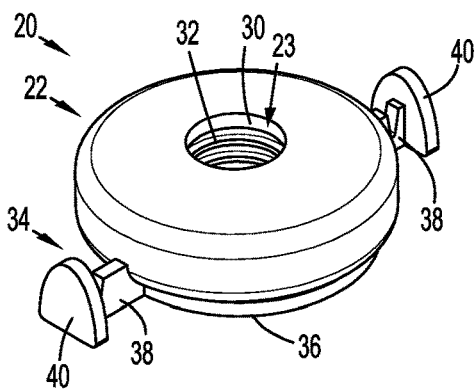
FIG. 3 is a perspective view of the retention anchor of FIG. 1.
Figure 4:
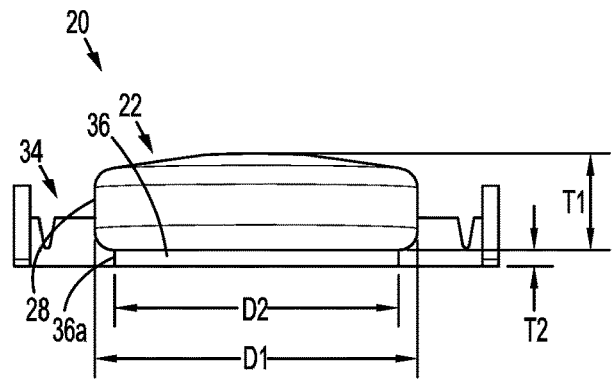
FIG. 4 is a side view of the retention anchor of FIG. 3.

Turning now to FIGS. 2-4, the retention anchor 20 includes an annular body 22 having a first or proximally-facing surface 24, a second or distally-facing surface 26, an outer side surface 28, and an inner side surface 30. The outer and inner side surfaces 28, 30 extend between and interconnect the first and second surfaces 24, 26. The inner side surface 30 defines an opening 23 extending longitudinally through the annular body 22 that is sized and shaped to accommodate the elongated shaft 12 of the cannula 10 in a friction fit manner.

The inner side surface 30 of the annular body 22 includes ridges 32 to enhance the grip of the annular body 22 about the elongated shaft 12 of the cannula 10 and to limit movement of the retention anchor 20 relative to the cannula 10. It should be understood that in addition or as an alternative to the ridges 32, the inner side surface 30 of the annular body 22 may include protrusions, bumps, projections, or other textured finishes to aid in frictionally retaining the retention anchor 20 on the elongated shaft 12 of the cannula 10 while allowing movement of the annular body 22 relative to the elongated shaft 12.

The retention anchor 20 includes a fixation body 34 affixed to the annular body 22 (e.g., by overmolding, solvent bonding, using adhesives, etc). The fixation body 34 includes a disc 36 and wings 38 extending outwardly from the disc 36 and terminating at flanges 40. A distal surface 34a of the fixation body 34, which is defined by portions of the disc 36, the wings 38, and the flanges 40, is planar for positioning against tissue.

The disc 36 is secured to the second surface 26 of the annular body 22 (e.g., using mechanical attachment features, such as tabs or pins, chemical attachment features, such as adhesives, or attachment methods, such as welding or overmolding). It is envisioned that the disc 36 may be disposed within the annular body 22 (e.g., the annular body 22 may be molded around disc 36).

The disc 36 includes an opening 37 defined therethrough that is aligned with the opening 23 of the annular body 22 to accommodate passage of the elongated shaft 12 of the cannula 10 therethrough. The disc 36 has an outer terminal edge 36a that is disposed radially inwardly of the outer side surface 28 of the annular body 22 such that a diameter "D1" of the annular body 22 is greater than a diameter "D2" of the disc 36. It should be understood that the outer terminal edge 36a of the disc 36 may be coincident with the outer side surface 28 of the annular body 22, or may extend radially outwardly of the outer side surface 28. The disc 36 is thin compared to the annular body 22 and has a thickness "T2" that is less than a thickness "T1" of the annular body 22. The disc 36 is of sufficient thickness "T2" to support the wings 38.

The wings 38 extend from opposed sides of the disc 36. While two wings 38 are shown, it is envisioned that the fixation body 34 may include more than two wings 38 (e.g., three wings or four wings or more) disposed radially around the disc 36 in substantially equally spaced relation relative to each other. Each wing 38 has a proximal facing surface 38a including a notch 39 defined therein. The notches 39 are sized and shaped to accommodate sutures 2 (FIG. 7) therein.

While a single notch 39 is shown in each wing 38, it is envisioned that each wing 38 may include a plurality of notches 39 (e.g., two notches or three notches or more) to accommodate, e.g., more than one suture and/or various suture sizes.

Each flange 40 extends proximally and laterally from the respective wing 38. The flanges 40 are sized and shaped (e.g., dome or semi-circular in shape) to retain the sutures 2 (FIG. 7) on the respective wing 38, for example, should the sutures 2 become disengaged from the notches 39. In some aspects, the wings 38 may not include the notches 39, and the sutures 2 are retained on the wings 38 via the flanges 40.

Figure 5:
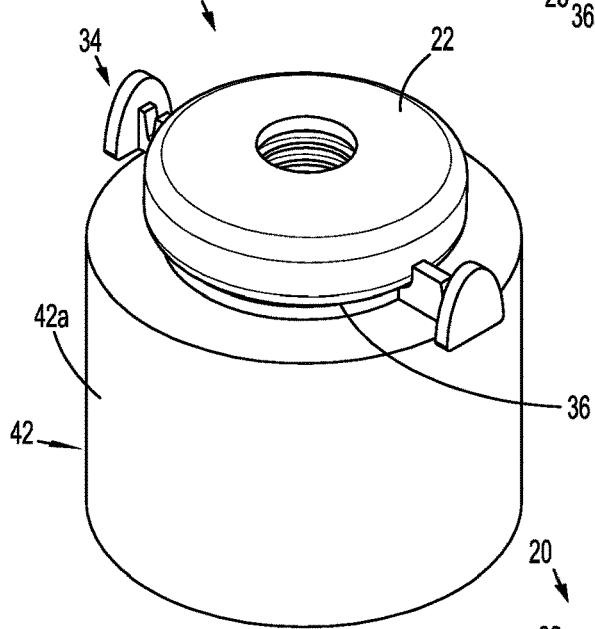
FIG. 5 is a perspective view of the retention anchor of FIG. 1, further including a compressible collar.
Figure 6:
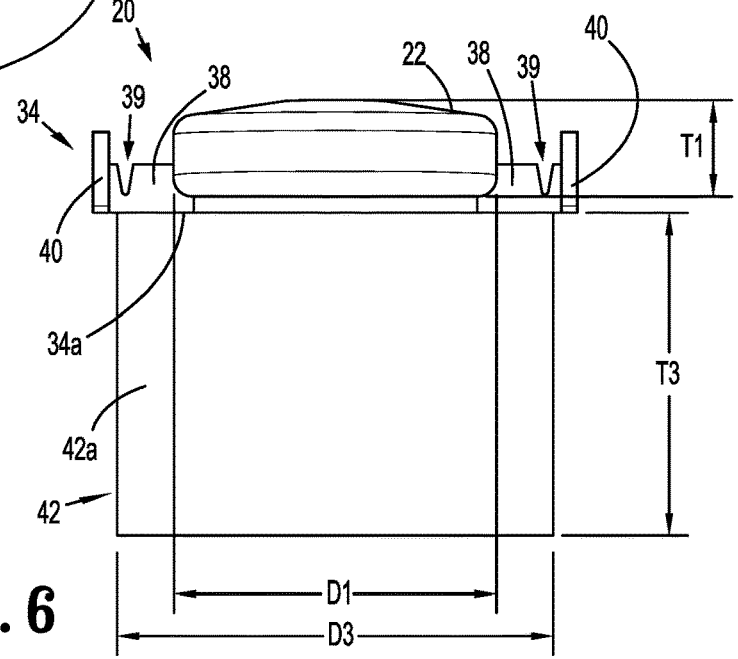
FIG. 6 is a side view of the retention anchor of FIG. 5.

Turning now to FIGS. 5 and 6, the retention anchor 20 further includes a compressible collar 42 affixed to the distal surface 34a of the fixation body 34. The compressible collar 42 may be secured to the fixation body 34 using fixation features such as those described above with regard to securing the disc 36 of the fixation body 34 to the annular body 22. The compressible collar 42 is capable of undergoing a change in shape between a first, expanded configuration, as shown in FIGS. 5 and 6, and a second, compressed configuration, as shown in FIG. 7.

The compressible collar 42 includes an opening (not explicitly shown) defined therethrough that is aligned with the openings 23, 37 (FIG. 2) of the annular body 22 and the fixation body 24 for reception and passage of the elongated shaft 12 of the cannula 10 therethrough. The compressible collar 42 includes an outer side surface 42a that is aligned with or disposed radially inwardly of the notches 39 defined in the wings 38 of the fixation body 34. A diameter "D3" of the compressible collar 42 is greater than the diameter "D1" of the annular body 22 and the compressible collar 42 is concentric with the annular body 22 such that the compressible collar 42 extends radially outwardly of the annular body 22. It is envisioned that the diameter "D3" of the compressible collar 42 may be the same as or less than the diameter "D1" of the annular body 22. A thickness "T3" of the compressible collar 42 is greater than the thickness "T1" of the annular body 22 when the compressible collar 42 is in the expanded configuration (FIG. 5), and the thickness "T3" is smaller or substantially the same as the thickness "T1" when the compressible collar 42 is in the compressed configuration (FIG. 7).

The annular body 22 is formed from a flexible material, such as a rubber or other suitable polymer (e.g., elastomers). The substrate 34 is formed from a material more rigid than the annular body 22, such as a plastic. The compressible collar 42 is formed from a compressible material, such as a foam, cotton or other suitable textile.

Figure 7:
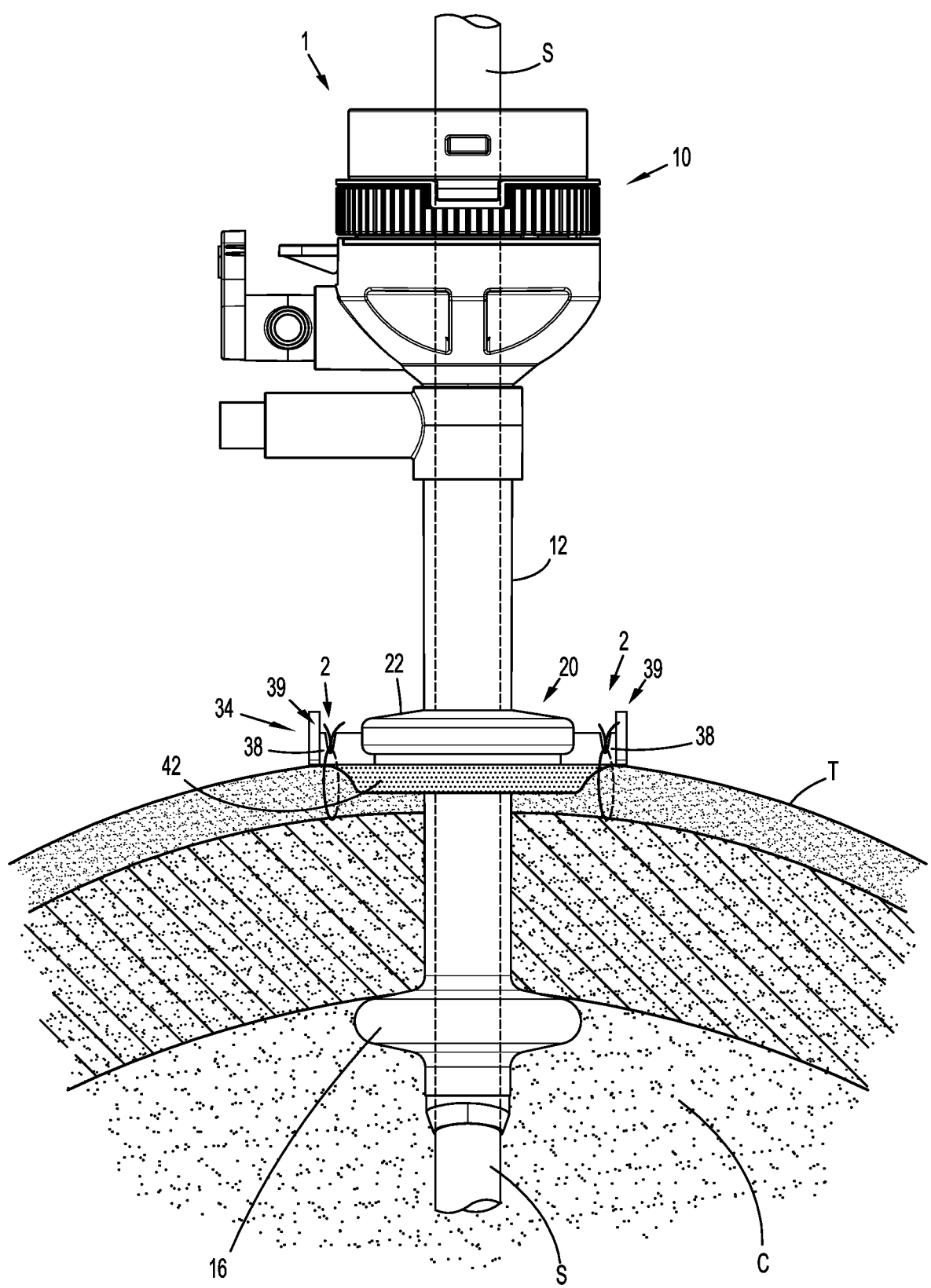
FIG. 7 is a side view of the surgical access assembly of FIG. 1, including the retention anchor of FIG. 5, shown secured to tissue.

FIG. 7 illustrates the surgical access assembly 1 disposed within tissue "T," e.g., an abdominal wall. The retention anchor 20 is secured to the cannula 10 prior to introducing the cannula 10 into the tissue "T" (e.g., the retention anchor 20 may be pre-installed on the cannula 10 during manufacture or may be placed on the cannula 10 prior to use in the operating room). The elongated shaft 12 of the cannula 10 is received through the tissue "T" (e.g., by utilizing an obturator (not shown) to facilitate entry of the cannula 10 through the tissue "T"), and the expandable anchor 16 is inflated within a body cavity "C" to prevent the cannula 10 from being withdrawn through the tissue "T."

The retention anchor 20 is slid distally along the elongated shaft 12 of the cannula 10 until the retention anchor 20 abuts or presses on the tissue "T." Specifically, as the retention anchor 20 is slid distally, the compressible collar 42, disposed in the expanded configuration (FIG. 5), contacts the tissue "T" and is compressed to the compressed configuration. Alternatively, in aspects where the retention anchor 20 does not include the compressible collar 42 (see e.g., FIG. 3), the retention anchor 20 is slid distally until the fixation body 34 contacts the tissue "T."

Sutures 2 which may be placed at the port site for closing the tissue "T" or as stay sutures, are passed around the wings 38 of the fixation body 34 and through the notches 39 of the wings 38. The tissue "T" is thus sandwiched between the expandable anchor 16 and the retention anchor 20, and secured to the retention anchor 20, to prevent the cannula 10 from being withdrawn from or over-inserted into the tissue "T." In this manner, the surgical access assembly 1 is secured to the tissue "T" and longitudinal movement of the cannula 10 relative to the tissue "T" is prevented or minimized throughout insertion, withdrawal, and/or manipulation of a surgical instrument "S" or a specimen through the cannula 10.

Following the surgical procedure, the expandable anchor 16 is deflated and the sutures 2 are cut to permit the withdrawal of the cannula 10 from the tissue "T." After the sutures 2 are disengaged from the retention anchor 20, the sutures 2 are removed or are used to close the tissue "T." The retention anchor 20 may remain secured to and disposed about the elongated shaft 12 of the cannula 10 during withdrawal of the cannula 10, or may be moved (e.g., slid proximally along the elongated shaft 12).

It should be understood that the surgical access assembly 1 is suitable for use in a variety of surgical procedures. For example, while the surgical access assembly 1 is shown with the expandable anchor 16 positioned within a body cavity "C" (e.g., within a peritoneum), the surgical access assembly 1 may be utilized in other ways, such as between layers of tissue "T" (e.g., extraperitoneally, such as in hernia procedures). In such procedures, the expandable anchor 16 is positioned between layers of the tissue "T" to dissect or separate the tissue "T," and the retention anchor 20 maintains the longitudinal position of the cannula 10 even if the cannula 10 is disposed at an angle with respect to the most proximal layer of the tissue "T" (e.g., not necessarily perpendicular to the tissue "T").

While aspects of the disclosure have been shown in the drawings, it is not intended that the disclosure be limited thereto, as it is intended that the disclosure be as broad in scope as the art will allow and that the specification be read likewise. It is to be understood, therefore, that the disclosure is not limited to the precise aspects described, and that various other changes and modifications may be effected by one skilled in the art without departing from the scope or spirit of the disclosure. Therefore, the above description should not be construed as limiting, but merely as exemplifications of aspects of the disclosure. Thus, the scope of the disclosure should be determined by the appended claims and their legal equivalents, rather than by the examples given

What is claimed is:

1. A surgical access assembly comprising:
 a cannula including an elongated shaft; and
 a retention anchor movably positionable along the elongated shaft, the retention anchor including:
 an annular body including a proximally-facing surface, a distally-facing surface, an inner side surface defining an opening through the annular body, and an outer side surface; and
 a fixation body including a disc having a proximal surface, a distal surface, and an outer terminal edge extending between the proximal surface and the distal surface, the proximal surface of the disc secured in touching contact to the distally-facing surface of the annular body, the fixation body including wings extending radially outwardly from the outer terminal edge of the disc beyond the outer side surface of the annular body, the disc defining an opening through the fixation body, the elongated shaft extending through the openings in the annular body and the fixation body.

2. The surgical access assembly of claim 1, wherein the inner side surface of the annular body frictionally engages the elongated shaft of the cannula.

3. The surgical access assembly of claim 2, wherein the inner side surface of the annular body includes ridges.

4. The surgical access assembly of claim 1, wherein each of the wings of the fixation body includes a notch defined in a proximal facing surface of the wing.

5. The surgical access assembly of claim 1, wherein each of the wings includes a flange disposed at a terminal end of the wing.

6. The surgical access assembly of claim 5, wherein a distal surface of the fixation body is planar and defined by portions of the disc, the wings, and the flanges.

7. The surgical access assembly of claim 1, wherein a distal surface of the fixation body is planar and defined by the distal surface of the disc and distal surfaces of the wings.

8. The surgical access assembly of claim 1, further including a compressible collar secured to a distal surface of the fixation body, the compressible collar having an expanded configuration and a compressed configuration.

9. The surgical access assembly of claim 8, wherein the compressible collar extends radially outwardly of the annular body and is concentric with the annular body.

10. The surgical access assembly of claim 8, wherein each of the wings of the fixation body includes a notch defined in a proximal facing surface of the wing, and the compressible collar is disposed radially inwardly of the notches.

11. The surgical access assembly of claim 1, wherein the fixation body is formed from a material that is more rigid than a material of the annular body.

12. The surgical access assembly of claim 1, wherein the outer terminal edge of the disc is disposed radially inwardly of the outer side surface of the annular body, and a thickness of the disc is less than a thickness of the annular body.

13. A retention anchor for a surgical access device, comprising:
   an annular body including a proximally-facing surface, a distally-facing surface, an inner side surface defining an opening through the annular body, and an outer side surface; and
   a fixation body including a disc having a proximal surface, a distal surface, and an outer terminal edge extending between the proximal surface and the distal surface, the proximal surface of the disc secured in direct abutting relationship to the distally-facing surface of the annular body the fixation body including wings extending radially outwardly from the outer terminal edge of the disc beyond the outer side surface of the annular body, the disc defining an opening through the fixation body, the elongated shaft extending through the openings in the annular body and the fixation body.

14. The retention anchor of claim 13, wherein the inner side surface of the annular body includes ridges.

15. The retention anchor of claim 13, wherein each of the wings of the fixation body includes a notch defined in a proximal facing surface of the wing.

16. The retention anchor of claim 13, wherein each of the wings includes a flange disposed at a terminal end of the wing.

17. The retention anchor of claim 13, wherein a distal surface of the fixation body is planar and defined by the distal surface of the disc and distal surfaces of the wings.

18. The retention anchor of claim 13, further including a compressible collar secured to a distal surface of the fixation body, the compressible collar having an expanded configuration and a compressed configuration.

19. The retention anchor of claim 18, wherein the compressible collar extends radially outwardly of the annular body and is concentric with the annular body.

20. The retention anchor of claim 18, wherein each of the wings of the fixation body includes a notch defined in a proximal facing surface of the wing, and the compressible collar is disposed radially inwardly of the notches.

* * * * *